US00PP16833P2

(12) United States Plant Patent
Vandenberg

(10) Patent No.: US PP16,833 P2
(45) Date of Patent: Jul. 18, 2006

(54) ***CHRYSANTHEMUM* PLANT NAMED 'YELLOW WATCH'**

(50) Latin Name: *Chrysanthemum×morifolium*
Varietal Denomination: Yellow Watch

(75) Inventor: Cornelis P. Vandenberg, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 12 days.

(21) Appl. No.: 11/122,802

(22) Filed: May 5, 2005

(51) Int. Cl.
*A01H 5/00* (2006.01)

(52) U.S. Cl. ..... Plt./289

(58) Field of Classification Search ..... Plt./289
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Chrysanthemum* plant named 'Yellow Watch', characterized by its upright cut *Chrysanthemum* that is usually grown as a disbud-type; dark green-colored foliage; decorative-type inflorescences; quill to spoon-shaped and bright yellow-colored ray florets; response time about 9.5 weeks; strong flowering stems; and good postproduction longevity.

2 Drawing Sheets

Botanical designation: *Chrysanthemum×morifolium.*
Cultivar denomination: 'Yellow Watch'.

BACKGROUND OF THE INVENTION

The present invention relates to a new and distinct cultivar of *Chrysanthemum* plant, botanically known as *Chrysanthemum×morifolium* and hereinafter referred to by the name 'Yellow Watch'.

The new *Chrysanthemum* is a naturally-occurring whole plant mutation of the *Chrysanthemum×morifolium* cultivar Watch, disclosed in U.S. Plant Pat. No. 13,463. The new *Chrysanthemum* was discovered and selected by the Inventor as a single flowering plant within a population of plants of the cultivar Watch in a controlled environment in Alva, Fla. in November, 2000. The selection of this plant was based on its unique and attractive ray floret coloration.

Asexual reproduction of the new *Chrysanthemum* by terminal cuttings in a controlled environment in Alva, Fla. since January, 2001, has shown that the unique features of this new *Chrysanthemum* are stable and reproduced true to type in successive generations.

SUMMARY OF THE INVENTION

Plants of the cultivar Yellow Watch have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yellow Watch'. These characteristics in combination distinguish 'Yellow Watch' as a new and distinct cultivar:

1. Upright cut *Chrysanthemum* that is usually grown as a disbud-type.
2. Dark green-colored foliage.

3. Large decorative-type inflorescences that are about 10.1 cm in diameter.
4. Attractive quill or spoon-shaped and bright yellow-colored ray florets.
5. Response time about 9.5 weeks.
6. Strong flowering stems.
7. Good postproduction longevity with inflorescences and foliage maintaining good substance and color for about three weeks in an interior environment.

Compared to plants of the parent, the cultivar Watch, plants of the new *Chrysanthemum* differ primarily in ray floret coloration as plants of the cultivar Watch have inflorescences with reddish brown centers which is enhanced by low production temperatures.

Plants of the new *Chrysanthemum* can be compared to plants of the *Chrysanthemum×morifolium* cultivar Treat, disclosed in U.S. Plant Pat. No. 14,788. In side-by-side comparisons conducted in Alva, Fla., plants of the new *Chrysanthemum* differed from plants of the cultivar Treat in the following characteristics:

1. Plants of the new *Chrysanthemum* had shorter but stronger flowering stems than plants of the cultivar Treat.
2. Plants of the new *Chrysanthemum* had smaller inflorescences than plants of the cultivar Treat.

BRIEF DESCRIPTION OF THE PHOTOGRAPHS

The accompanying colored photographs illustrate the overall appearance of the new *Chrysanthemum,* showing the colors as true as it is reasonably possible to obtain in colored reproductions of this type. Colors in the photographs may differ slightly from the color values cited in the detailed botanical description which accurately describe the colors of the new *Chrysanthemum.*

The photograph on the first sheet comprises a side perspective view of a typical flowering stem of 'Yellow Watch' grown as a disbud-type.

The photograph on the second sheet comprises a close-up view of a typical inflorescence of 'Yellow Watch'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Salinas, Calif., under conditions which approximate commercial practice in a polyethylene-covered greenhouse. Two-week old rooted cuttings were planted on Nov. 3, 2004 and received four weeks of long day/short nights followed by short day/long nights until flowering. Plants were grown as single-stem disbud-type cut *Chrysanthemums*. During the production time, the following environmental conditions were measured: day temperatures, 24 to 27° C.; night temperatures, 10 to 16° C.; and light levels, 2,000 to 4,000 foot-candles. Measurements and numerical values represent averages for six to ten typical flowering stems and were taken about ten weeks after the start of short days.

Botanical classification: *Chrysanthemum×morifolium* cultivar Yellow Watch.

Commercial classification: Decorative-type cut *Chrysanthemum*.

Parentage: Naturally-occurring whole plant mutation of the *Chrysanthemum×morifolium* cultivar Watch, disclosed in U.S. Plant Pat. No. 13,463.

Propagation:

*Type.*—Terminal tip cuttings.

*Time to rooting.*—About 10 to 14 days with soil temperatures of 18 to 21° C.

*Root description.*—Fine, fibrous; white in color.

*Rooting habit.*—Freely branching.

Plant description:

*Appearance.*—Herbaceous decorative-type cut flower that is typically grown as a disbud-type.

*Flowering stem description.*—Aspect: Erect. Length: About 109 cm. Stem diameter: About 7 mm. Internode length: About 3.7 cm. Texture: Pubescent; longitudinally ridged. Color: Close to 146A overlain with close to 187A.

*Foliage description.*—Arrangement: Alternate. Length: About 9.1 cm. Width: About 5.2 cm. Apex: Cuspidate. Base: Attenuate. Margin: Palmately lobed; sinuses mostly divergent. Texture: Upper and lower surfaces, pubescent and leathery; veins prominent on lower surface. Color: Developing and fully expanded foliage, upper surface: Close to 147A. Developing and fully expanded foliage, lower surface: Close to 147B. Venation, upper surface: Close to 147A. Venation, lower surface: Close to 147B to 146A. Petiole: Length: About 2.4 cm. Diameter: About 3 mm. Texture, upper and lower surfaces: Pubescent. Color, upper and lower surfaces: 146A to 146B.

Flowering description:

*Appearance.*—Decorative-type inflorescence form with quilled or spoon-shaped ray florets. Inflorescences borne on terminals, arising from leaf axils. Ray florets develop acropetally on a capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to three to four weeks of long day/short night conditions after planting followed by photoinductive short day/long night conditions flower about 9.5 weeks later when grown as a disbud-type.

*Postproduction longevity.*—In an interior environment, inflorescences and foliage will maintain good color and substance for about three weeks in an interior environment.

*Quantity of inflorescences.*—Grown as a disbud-type, only one inflorescence is allowed to develop.

*Fragrance.*—Faint, sweet.

*Inflorescence size.*—Diameter: Large, about 10.1 cm. Depth (height): About 3.2 cm. Disc diameter: None observed. Receptacle diameter: About 1.1 cm. Receptacle height: About 9 mm.

*Inflorescence buds.*—Height: About 7.5 mm. Diameter: About 1 cm. Shape: Oblate. Color: Close to 146A.

*Ray florets.*—Shape: Quilled or spoon-shaped. Length: About 5.1 cm. Width, apex: About 5 mm. Width, tube: About 3 mm. Corolla tube length: About 4 cm. Apex: Emarginate or acute. Base: Fused. Texture: Smooth, glabrous; satiny; longitudinally ridged. Aspect: Initially erect; when mature, mostly straight and eventually perpendicular to the peduncle. Number of ray florets per inflorescence: About 324 in numerous whorls. Color: When opening, upper and lower surfaces: Close to 6A to 9A. Fully opened, upper and lower surfaces: Close to 6B to 9B.

*Phyllaries.*—Quantity per inflorescence: About 38 in about three whorls. Length: About 1.1 cm. Width: About 4 mm. Shape: Lanceolate. Apex: Acute. Base: Truncate. Margin: Entire. Texture, upper surface: Smooth, waxy. Texture, lower surface: Pubescent. Color, upper surface: Close to 146A. Color, lower surface: Close to 146A to 147A.

*Reproductive organs.*—Gynoecium: Style length: About 9 mm. Style color: Close to 144A to 144B. Stigma color: Close to 9A.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of 7° C. and high temperatures high temperatures of 38° C.

It is claimed:

1. A new and distinct cultivar of *Chrysanthemum* plant named 'Yellow Watch', as illustrated and described.

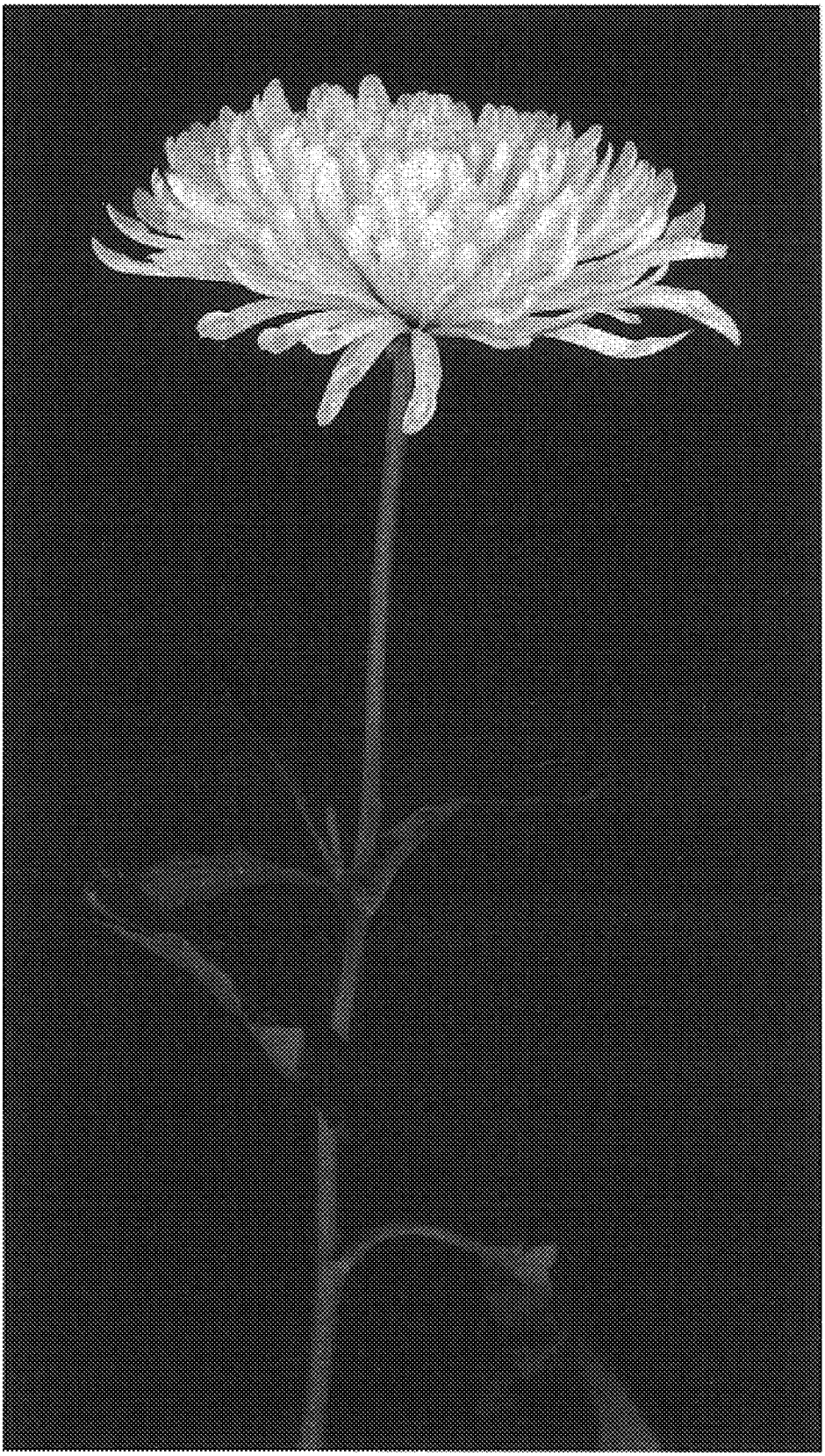

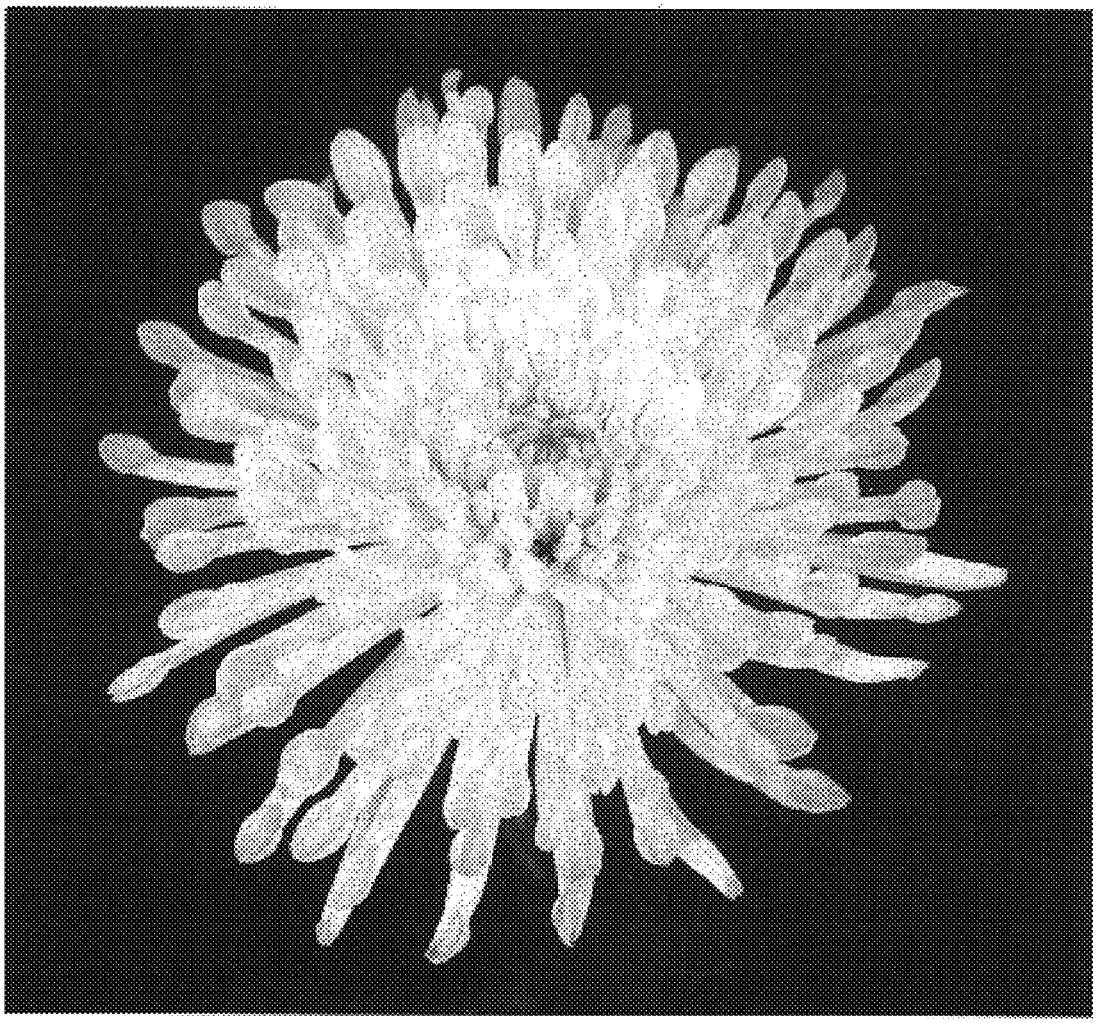

* * * * *